(12) United States Patent
Chiang et al.

(10) Patent No.: US 11,911,664 B2
(45) Date of Patent: Feb. 27, 2024

(54) CUSHION PAD

(71) Applicant: Global Esprit Inc., New Taipei (TW)

(72) Inventors: Herman Chiang, New Taipei (TW);
Tsai-Tung Wang, New Taipei (TW)

(73) Assignee: GLOBAL ESPRIT INC., New Taipel (TW)

( * ) Notice: Subject to any disclaimer, the term of this patent is extended or adjusted under 35 U.S.C. 154(b) by 0 days.

(21) Appl. No.: 17/577,041

(22) Filed: Jan. 17, 2022

(65) Prior Publication Data
US 2023/0138929 A1    May 4, 2023

(30) Foreign Application Priority Data
Oct. 29, 2021    (TW) .................................. 110212808

(51) Int. Cl.
*A63B 33/00*    (2006.01)
*A61F 9/02*    (2006.01)

(52) U.S. Cl.
CPC ............ *A63B 33/004* (2020.08); *A61F 9/026* (2013.01)

(58) Field of Classification Search
CPC ..... A61F 9/026; A63B 33/002; A63B 33/004; B63C 11/12
See application file for complete search history.

(56) References Cited

U.S. PATENT DOCUMENTS

| | | | | |
|---|---|---|---|---|
| 6,505,353 | B2* | 1/2003 | Sung | A63B 33/006 2/428 |
| 7,210,175 | B2* | 5/2007 | Chiang | A63B 33/004 2/450 |
| 7,891,024 | B2* | 2/2011 | Garofalo | B63C 11/12 2/439 |
| 9,156,532 | B2* | 10/2015 | Shiue | B63C 11/12 |
| 9,663,204 | B2* | 5/2017 | Kuroda | B63C 11/12 |
| 9,770,628 | B2* | 9/2017 | Shiue | A63B 33/004 |
| 10,206,819 | B2* | 2/2019 | Chiang | A63B 33/004 |
| 10,493,325 | B2* | 12/2019 | Chiang | A63B 71/10 |
| 10,576,333 | B2* | 3/2020 | Chiang | A63B 33/004 |
| 10,603,548 | B2* | 3/2020 | Chiang | A63B 33/004 |
| 10,668,326 | B2* | 6/2020 | Chiang | A63B 33/004 |
| 2017/0252609 | A1* | 9/2017 | Chiang | A61F 9/026 |
| 2022/0017190 | A1* | 1/2022 | Godoy | B63C 11/12 |

* cited by examiner

*Primary Examiner* — F Griffin Hall
(74) *Attorney, Agent, or Firm* — Cheng-Ju Chiang (57) ABSTRACT

A cushion pad assembled on a frame of a swimming goggles is provided, which includes a connecting portion that has an inner peripheral surface and outer peripheral surface, and a face-attaching portion that is connected to the connecting portion and has an outer ring surface and an inner ring surface. The cushion pad is characterized in that: the inner ring surface of the face-attaching portion is of a wavy curve that conforms to the depth and height of the outer periphery of the eye socket. A plurality of independent buffering bodies are provided between the outer peripheral surface of the connecting portion and the outer ring surface of the face-attaching portion, and each of the buffering bodies is jointly composed of a first supporting member, a second supporting member and a joint at an intersection of the first supporting member and the second supporting member.

6 Claims, 12 Drawing Sheets

CUSHION PAD

BACKGROUND OF INVENTION

1. Field of Invention

The present invention disclosure relates to a kind of pad, and more particularly, to a kind of pad dedicated to swimming goggles which can conform to the contour of the outer periphery of the eye socket after wearing, so as to absorb different squeezing and adsorption forces.

2. Related Art

Figure 1:
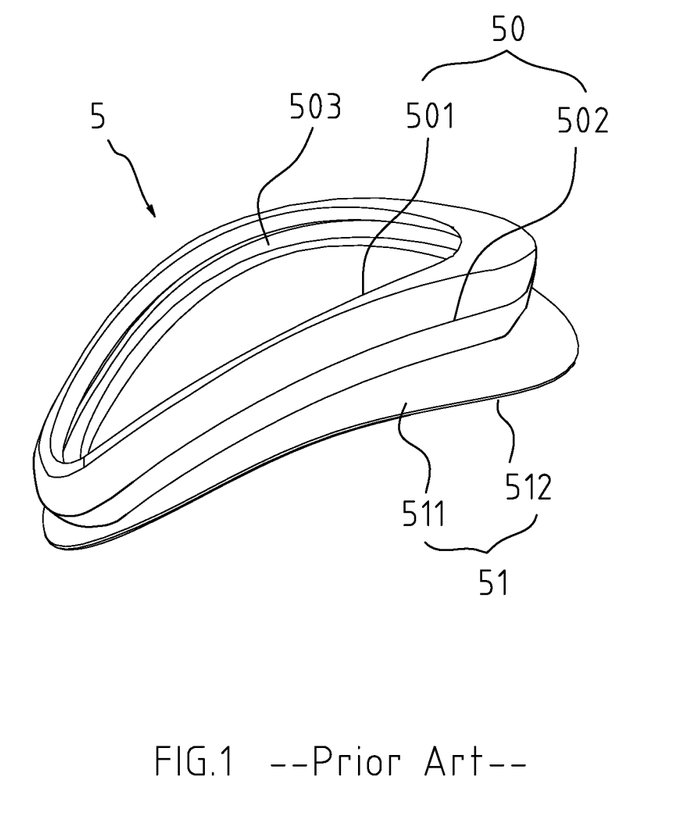
FIG. 1 is a perspective view of the related art cushion pad.

The function of swimming goggles is mainly to protect the eyes while swimming. Therefore, the anti-seepage design is an extremely important consideration. The cushion pad on the swimming goggles is to fit the eye socket to achieve the anti-seepage effect. The design of the protection pad is roughly divided into the foam type and cushion pad type. Among them, the cushion pad related to the present invention disclosure is to achieve the anti-seepage effect by squeezing and absorbing. Please refer to FIG. 1, the related art cushion pad 5 has a connecting portion 50 and a face-attaching portion 51, wherein the connecting portion 50 has an inner peripheral surface 501 and an outer peripheral surface 502. The inner peripheral surface 501 is provided with a groove 503 for assembling with the frame of swimming goggles (not shown in the figure). The face-attaching portion 51 has an outer ring surface 511 and an inner ring surface 512, The face-attaching portion 51 is squeezed and deformed during wearing, so that the space between the side of the inner ring surface 512 and the frame generates suction to be adsorbed around the eye socket. However, since the compressing deformation of the face-attaching portion 51 is directly stressed on the outer periphery of the eye socket, the pressure on the outer periphery of the eye socket is direct and obvious. In particular, the outer periphery of the eye socket has a contour with variation in depth and height, and therefore the headband of the swimming goggles must be tightened with greater tightening force to make the face-attaching portion 51 attach to the contour of the outer periphery of the eye socket, otherwise it will not fit the contour of the eye socket and there will be a risk of water seepage. However, the squeezing and adsorption caused by a large tightening force produces pressure on the outer periphery of the eye socket can affect the blood circulation around the eye socket, which discomforts the user and the effect of "panda eyes" may be seen on the user.

3. SUMMARY OF INVENTION

An objective of the present invention disclosure is to provide a cushion pad assembled on the frame of swimming goggles, which can provide different buffering resilience to different contact points on the periphery of the eye socket upon wearing the swimming goggles, so as to conform to the contour of the outer periphery of the eye socket, and absorb different squeezing and adsorption forces after wearing, in order to reduce an impact on contour of the outer periphery of the eye socket and prevent water seepage.

To achieve the above objective, the present invention disclosure provides a cushion pad assembled on a frame of a swimming goggles. The cushion pad comprises a connecting portion and a face-attaching portion, the connecting portion has an inner peripheral surface and an outer peripheral surface, the inner peripheral surface is provided with a groove for assembling with the frame of the swimming goggles; the face-attaching portion has an outer ring surface and an inner ring surface, the outer ring surface of the face-attaching portion is connected with the outer peripheral surface of the connecting portion, the inner ring surface of the face-attaching portion is arranged to contact with around an outer periphery of the eye socket, and the cushion pad is characterized in that:

An inner ring surface of the face-attaching portion conforms to the depth and the height of the wavy curve of the outer periphery of the eye socket. That is, a first peak of the inner ring surface corresponds to a center of a brow, a second peak of the inner ring surface corresponds to a cheekbone, a first valley of the inner ring surface corresponds to an eye corner, and a second valley of the inner ring surface corresponds to a nose bridge, so that a slope of a wavy curve is formed along the first peak at the center of the brow, the first valley at the eye corner, and the second peak at the cheekbone to the second valley of the nose bridge.

A plurality of independent buffering bodies are provided between the outer peripheral surface of the connecting portion and the outer ring surface of the face-attaching portion, wherein each of the buffering bodies is jointly composed of a first supporting member, a second supporting member and a joint at an intersection of the first supporting member and the second supporting member. By independent actions of each buffering body, the face-attaching portion has different buffering resilience to different contact points on the periphery of the eye socket; and with the first supporting member, the second supporting member and the joint of each of the buffering bodies absorbing a force that squeezes and deforms different stress locations of the inner ring surface of the face-attaching portion, so as to conform to the contour of the outer periphery of the eye socket, and absorb different squeezing and adsorption forces upon wearing the swimming goggles, in order to reduce an impact on contour of the outer periphery of the eye socket and prevent water seepage.

According to the aforementioned, wherein the first supporting member, the second supporting member and the joint jointly form a plurality of V-shaped buffering bodies on a side-view perspective; two wings and an intersection point of each of the V-shaped buffering bodies are the first supporting member, the second supporting member and the joint respectively, and the first supporting member and the second supporting member of each of the V-shaped buffering bodies connected with the outer peripheral surface of the connecting portion and the outer ring surface of the face-attaching portion respectively.

According to the aforementioned, wherein the first supporting member and second supporting member of the V-shaped buffering bodies arranged to be different in length so as to conform the depth and height of the outer periphery of the eye socket which is of the wavy curve, in which the side of V-shaped buffering bodies near the outer peripheral surface of the connecting portion is shorter than the side of V-shaped buffering bodies near a side of the outer ring surface of the face-attaching portion, so as to conform to the contour of the outer periphery of the eye socket, and absorb different squeezing and adsorption forces upon wearing the swimming goggles.

According to the aforementioned, wherein the openings of the V-shaped buffering bodies are arranged off an axis determined by a line connecting the center of the brow and the cheekbone.

According to the aforementioned, wherein the first supporting member, the second supporting member and the joint jointly form a hexagonal buffering body from a side view perspective, in which three sides of the hexagonal buffering body constitute the first supporting member, the other three sides of the hexagonal buffering body constitute the second supporting member, the six sides of the hexagonal buffering body form a plurality of joints, and two opposite joints of the hexagonal buffering bodies are respectively connected with the outer peripheral surface of the connecting portion and the outer ring surface of the face-attaching portion.

DESCRIPTION OF PREFERRED EMBODIMENTS

Figure 2A:
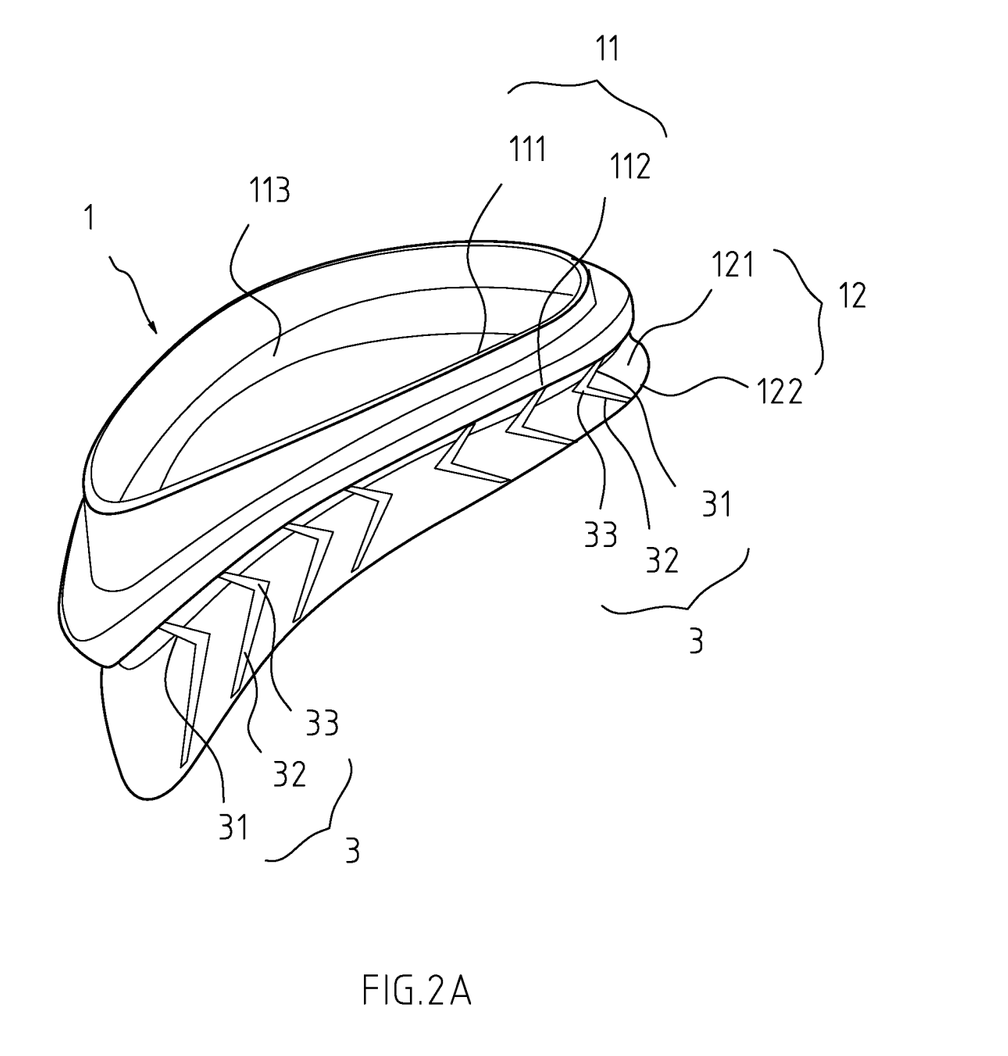
FIGS. 2A to 2C respectively are a perspective view, top view and bottom view of the cushion pad according to a first embodiment of the present invention disclosure.
Figure 2B:
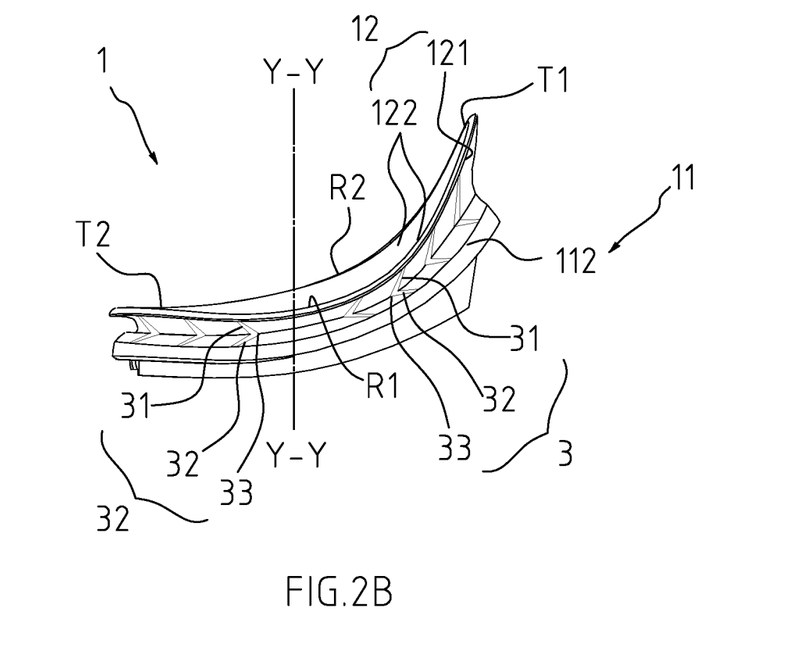
Figure 2C:
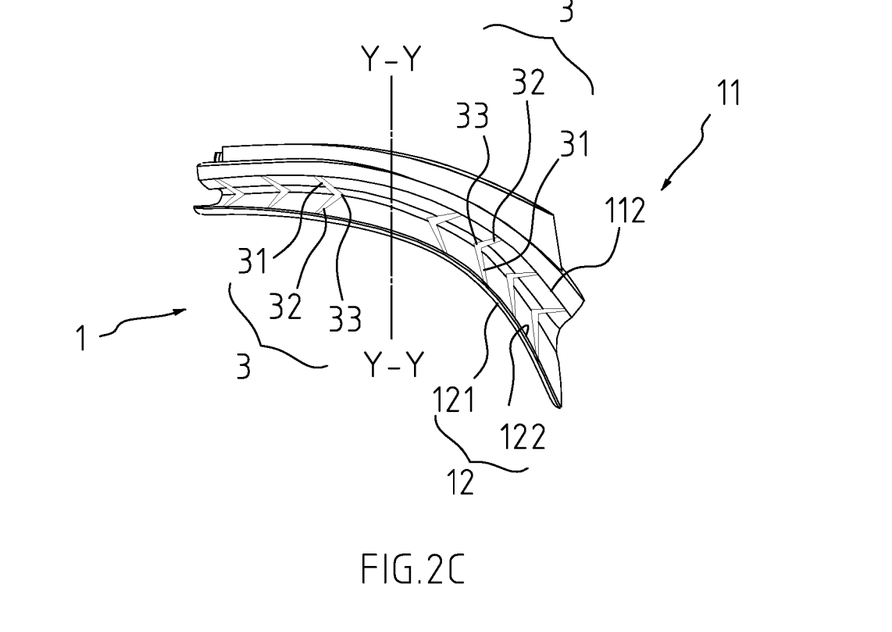

Please refer to FIG. 2A to FIG. 2C, which respectively are a stereoscopic view, top view and bottom view of the cushion pad according to a first embodiment of the present invention disclosure. As shown in FIG. 2A, the cushion pad 1 provided by the present invention disclosure comprises a connecting portion 11 and a face-attaching portion 12. The connecting portion 11 and the face-attaching portion 12 are made of thermoplastic rubber (TPR) or silicone, and the material of the connecting portion 11 is harder than that of the face-attaching portion 12. The connecting portion 11 has an inner peripheral surface 111 and an outer peripheral surface 112. The inner peripheral surface 111 is provided with a groove 113 for assembling with the frame 4 of the swimming goggles, which can be referred to FIG. 3 to FIG. 6. The face-attaching portion 12 has an outer ring surface 121 and an inner ring surface 122. The outer ring surface 121 is connected with the outer peripheral surface 112 of the connecting portion 11. The inner ring surface 122 is arranged to contact the periphery of the eye socket, and conform to the depth and the height of the wavy curve of the outer periphery of the eye socket, as shown in FIG. 2B. A first peak R1 of the inner ring surface 122 corresponds to a center of a brow, a second peak R2 of the inner ring surface corresponds to a cheekbone, a first valley T1 of the inner ring surface 122 corresponds to an eye corner, and a second valley T2 of the inner ring surface 122 corresponds to a nose bridge, so that a slope of a wavy curve is formed along the first peak R1 at the center of the brow, the first valley T1 at the eye corner, and the second peak R2 at the cheekbone to the second valley T2 of the nose bridge. This provides a natural fit contact with the outer periphery of the eye socket.

Please refer to FIGS. 2B and 2C, a plurality of independent buffering bodies 3 are provided between the outer peripheral surface 112 of the connecting portion 11 and the outer ring surface 121 of the face-attaching portion 12, each of the buffering bodies 3 comprises a first supporting member 31, a second supporting member 32, and a joint 33. In this embodiment, the first supporting member 31, the second supporting member 32 and the joint 33 jointly form a buffering body 3, presented in a V-shape from the side view perspective. The openings of the V-shaped buffering bodies 3 are arranged off the axis Y-Y determined by a line connecting the center of the brow and the cheekbone. Two wings and an intersection point of each of the V-shaped buffering bodies are the first supporting member, the second supporting member and the joint respectively. When being manufactured, the first supporting member 31 and the second supporting member 32 of each of the V-shaped buffering bodies 3 are connected with the outer peripheral surface 112 of the connecting portion 11 and the outer ring surface 121 of the face-attaching portion 12, respectively. Each of V-shaped buffering bodies 3 goes thinner from the joint 33 to the first supporting member 31 and to the second supporting member 32, and is thickest at the joint 33. Further, the first supporting member 31 and second supporting member 32 of the V-shaped buffering bodies 3 arranged to be different in length so as to conform the depth and height of the outer periphery of the eye socket which is of the wavy curve. That is, the first supporting member 31 on the side of V-shaped buffering bodies 3 near the outer peripheral surface 112 of the connecting portion 11 is shorter, steeper and thicker than the second supporting member 32 on the side of V-shaped buffering bodies 3 near a side of the outer ring surface 121 of the face-attaching portion 12, so as to conform to the contour of the outer periphery of the eye socket, and absorb different squeezing and adsorption forces upon wearing the swimming goggles.

Figure 3:
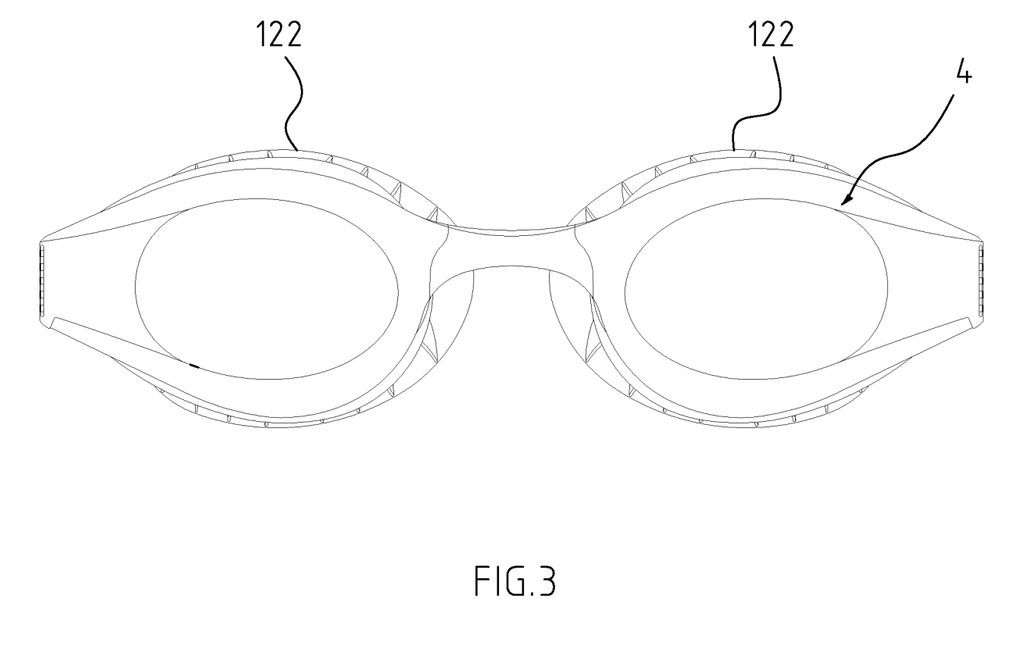
FIGS. 3 to 6 respectively are a front view, side view, top view and bottom view of the cushion pad assembled on the frame of swimming goggles according to the first embodiment of the present invention disclosure.
Figure 4:
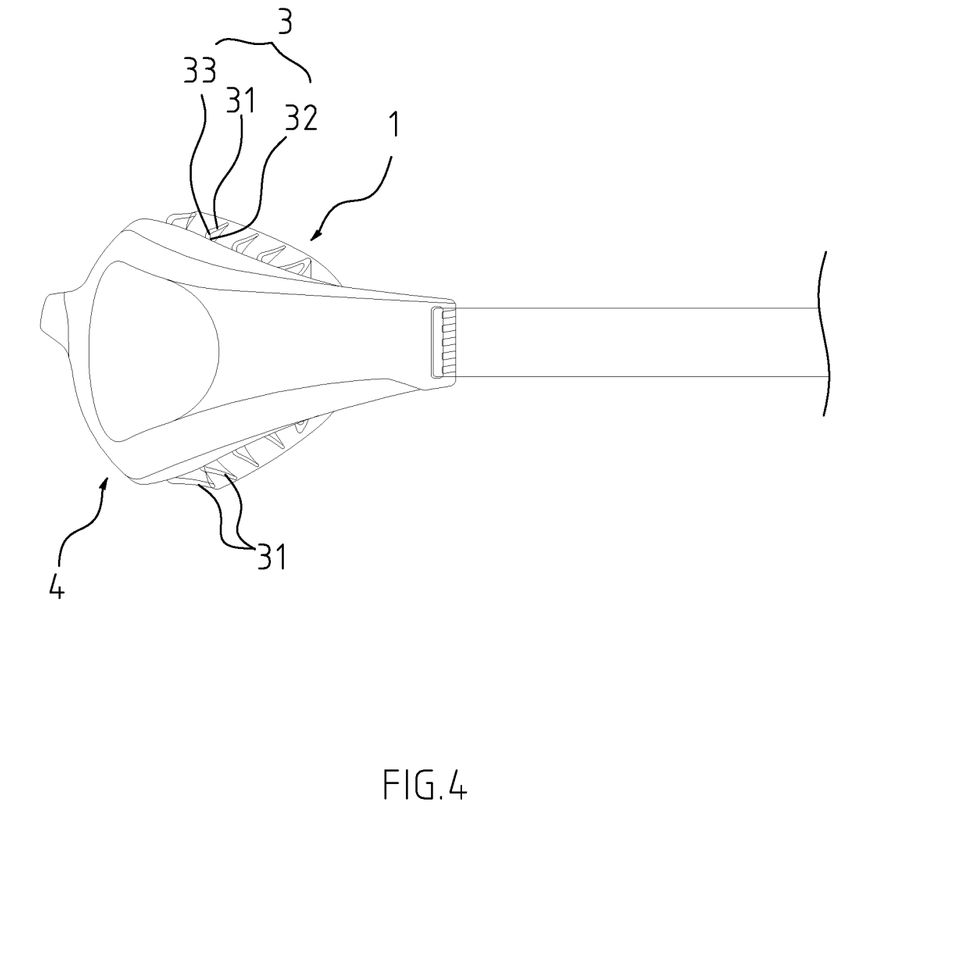
Figure 5:
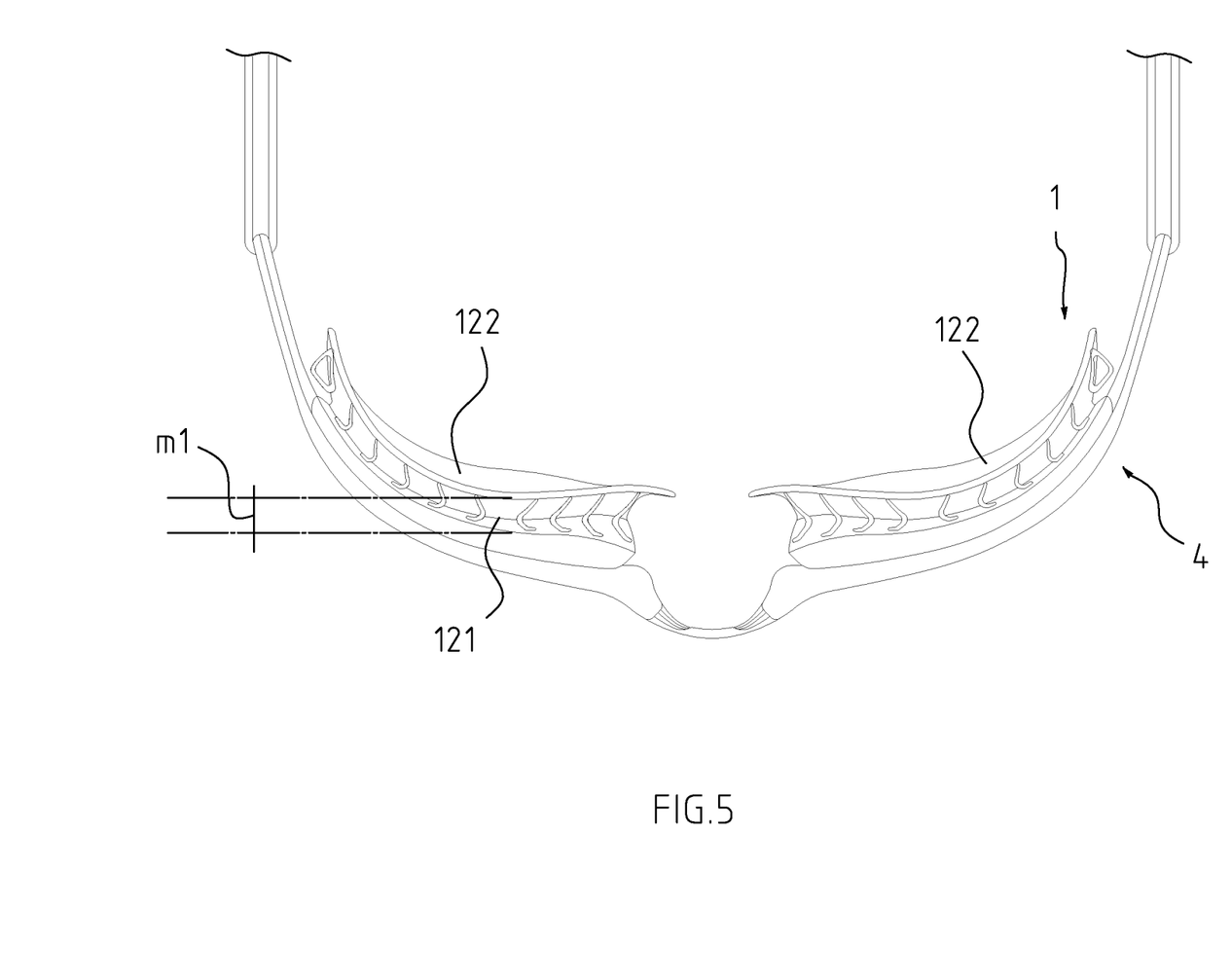
Figure 6:
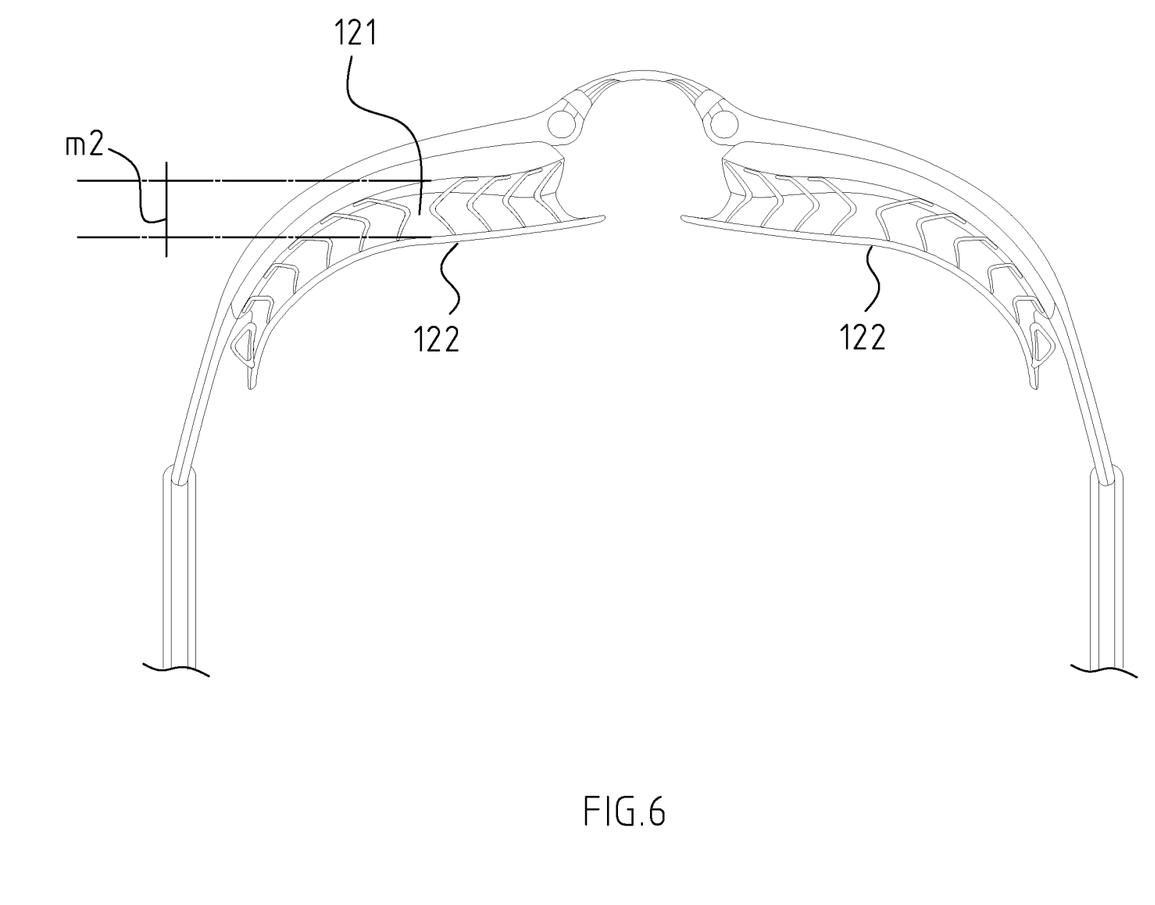

Please refer to FIG. 3, FIG. 5 and FIG. 6, which respectively are a front view, top view and bottom view of the cushion pad assembled on the frame of swimming goggles according to the first embodiment of the present invention disclosure. As shown in these figures, the wavy curve of the inner ring surface 122 can be seen from FIG. 5. The position indicated by the thickness m1 of the outer ring surface 121 when worn on the face is near the eyebrows, where the eye socket is relatively protruding at the position indicated by the thickness m1. As shown in FIG. 6, the position indicated by the thickness m2 of the outer ring surface 121 when worn on the face is near the eye bags, where the eye socket relatively concaving at the position indicated by the thickness m2. Accordingly, the thickness m2 is larger than the thickness m1, the entire inner ring surface 122 is formed in a wavy shape conforming to the contour of the eye socket, so as to naturally fit the outer periphery of the eye socket upon wearing, reducing the tightening force of the headband of the swimming goggles, and making it more comfortable to wear.

As shown in FIG. 2A, a plurality of independent buffering bodies 3 are provided between the outer peripheral surface 112 of the connecting portion 11 and the outer ring surface 121 of the face-attaching portion 12. Each of the buffering bodies 3 comprises a first supporting member 31 and a second supporting member 32, and a joint 33. With the arrangement of the first supporting member 31 and the second supporting member 32 on both sides of the V-shaped buffering bodies 3 which conforms to the depth and height of the wavy contour of the outer periphery of the eye socket to correspond to the eyebrows of the eye socket and the first supporting member 31 of the V-shaped buffering bodies 3 at the eye corner, compared with the second supporting member 32 of the V-shaped buffering bodies 3 corresponding to the cheekbones of the eye socket and the nose bridge, the first supporting member 31 is shorter, steeper, and thicker. Thus, the contour of the outer periphery of the eye socket can be conformed, so as to absorb different squeezing and adsorption forces upon wearing.

With the above mechanism, when the cushion pad 1 is assembled with the frame of the swimming goggles upon wearing, with the wavy curve of the inner ring surface 122 fittingly attaching the outer periphery of the eye socket in a natural manner, and with the first supporting member 31, the second supporting member 32 and the joint 33 of each of the buffering bodies 3 conforming to the contour of outer periphery of the eye socket, different squeezing and adsorption forces upon wearing the swimming goggles can be absorbed, in order to reduce an impact on contour of the outer periphery of the eye socket and thus prevent water seepage.

Figure 7:
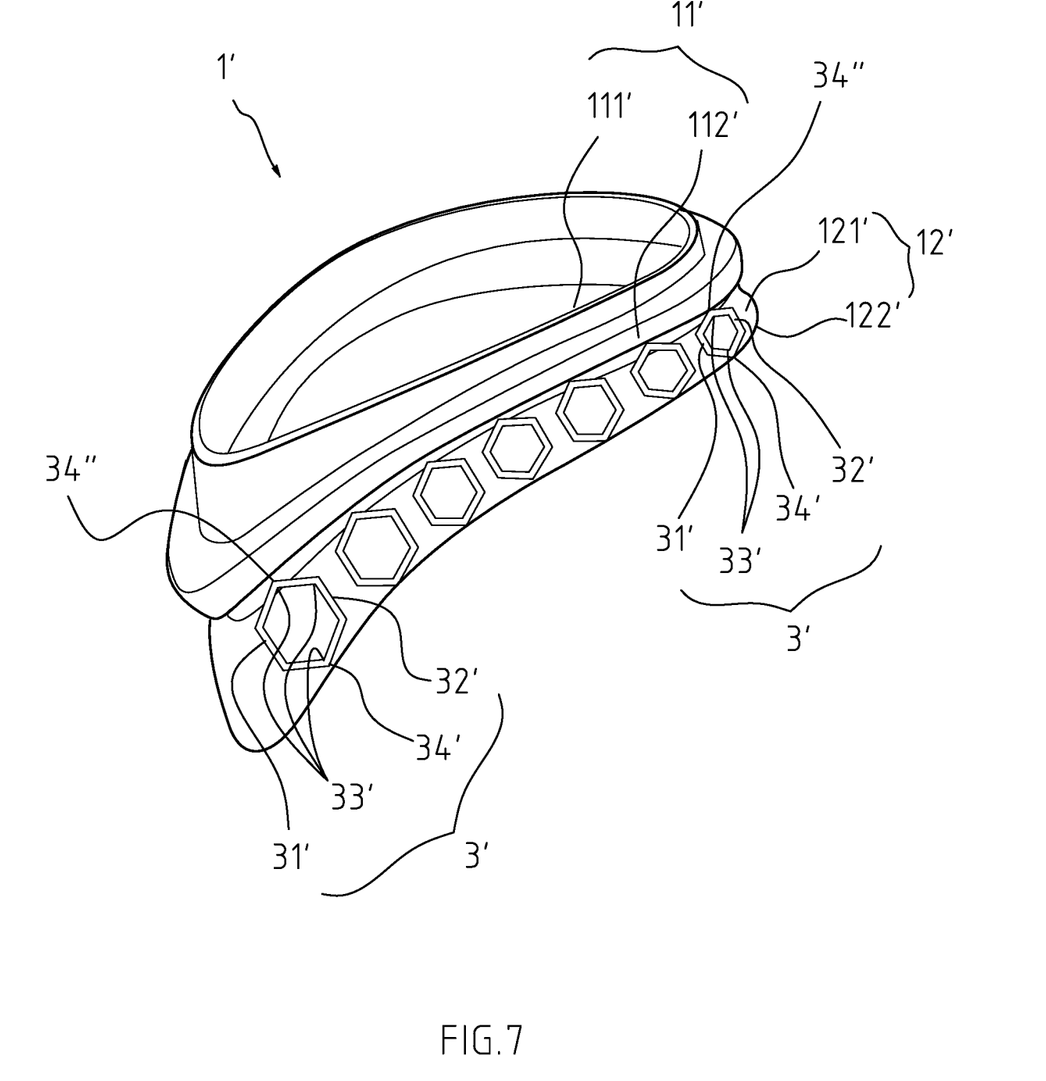
FIGS. 7 to 11 respectively are a stereoscopic view, front view, side view, top view and bottom view of the cushion pad assembled on the frame of swimming goggles according to a second embodiment of the present invention disclosure.
Figure 8:
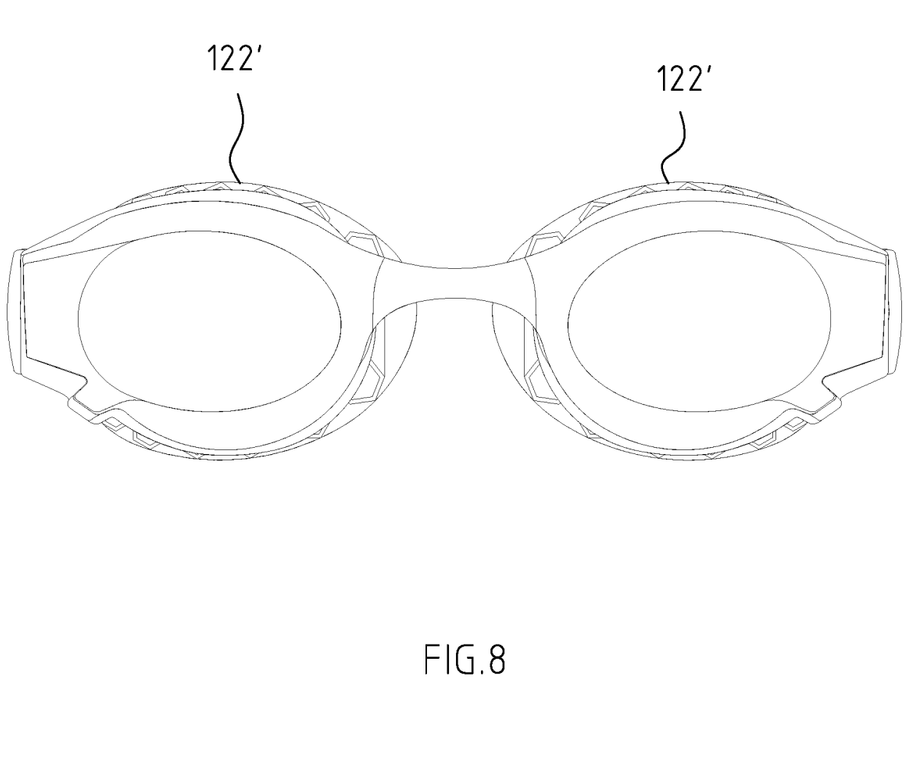
Figure 9:
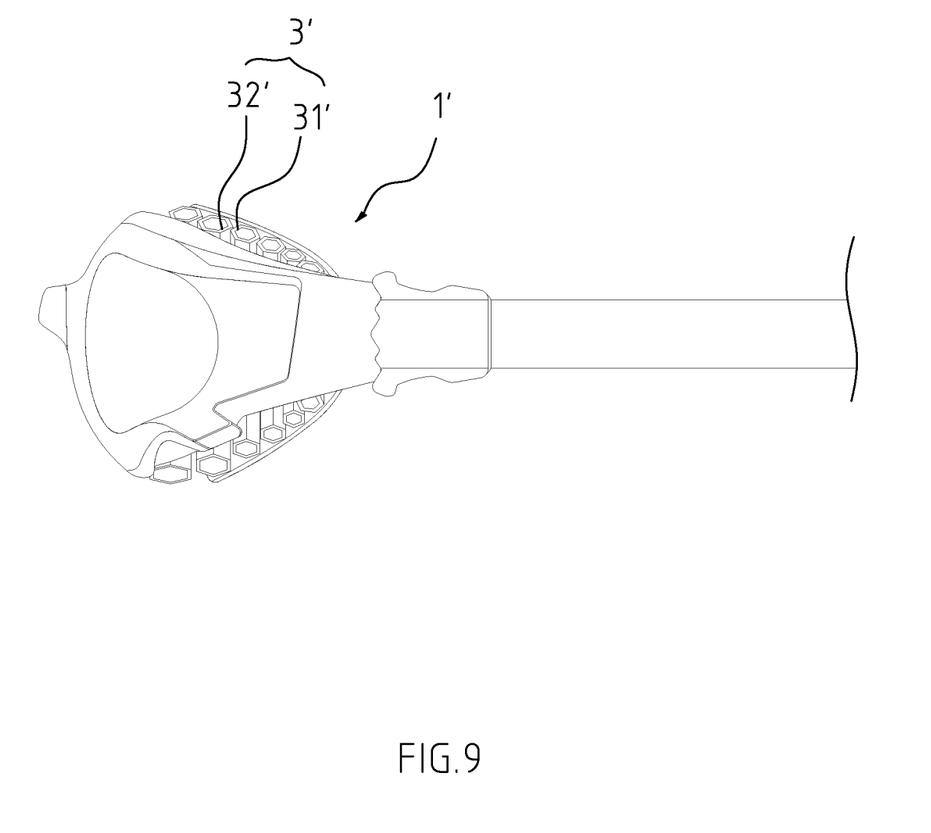
Figure 10:
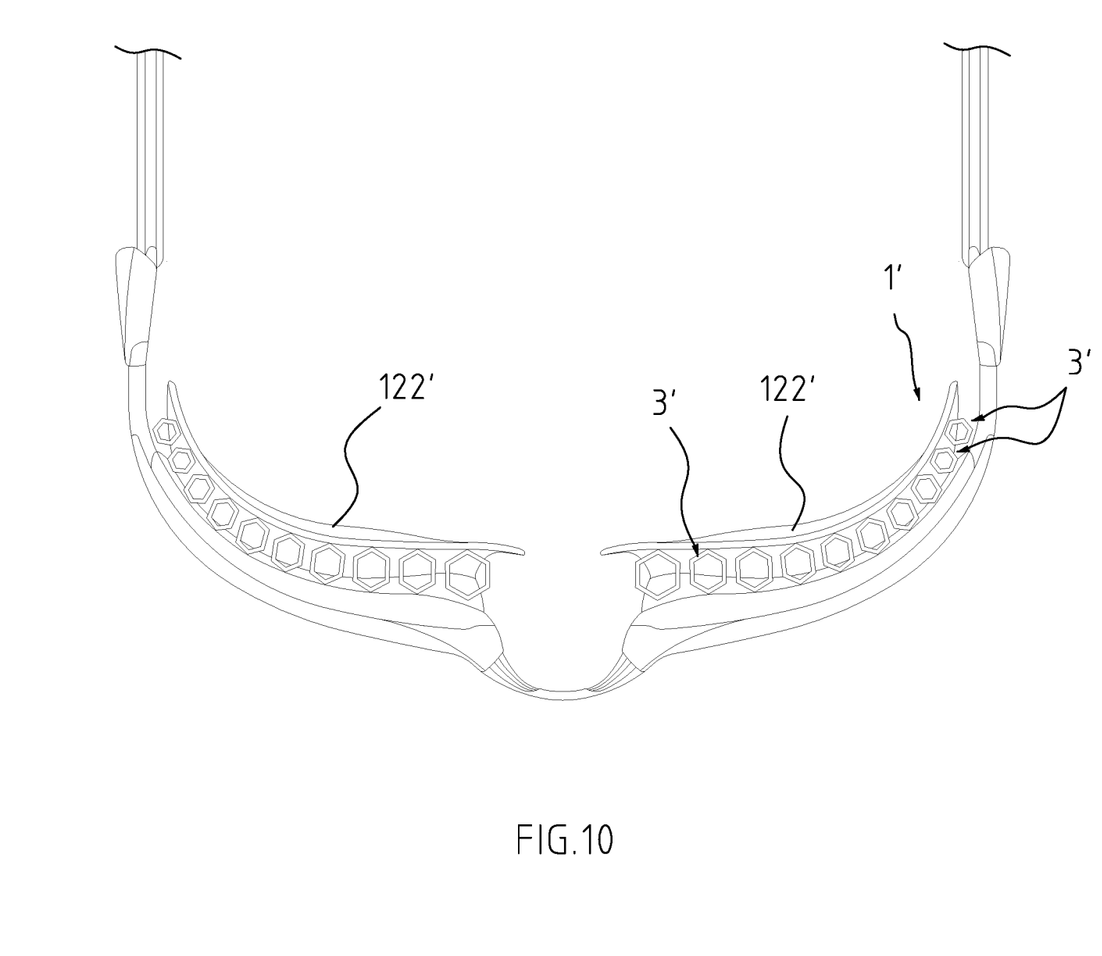
Figure 11:
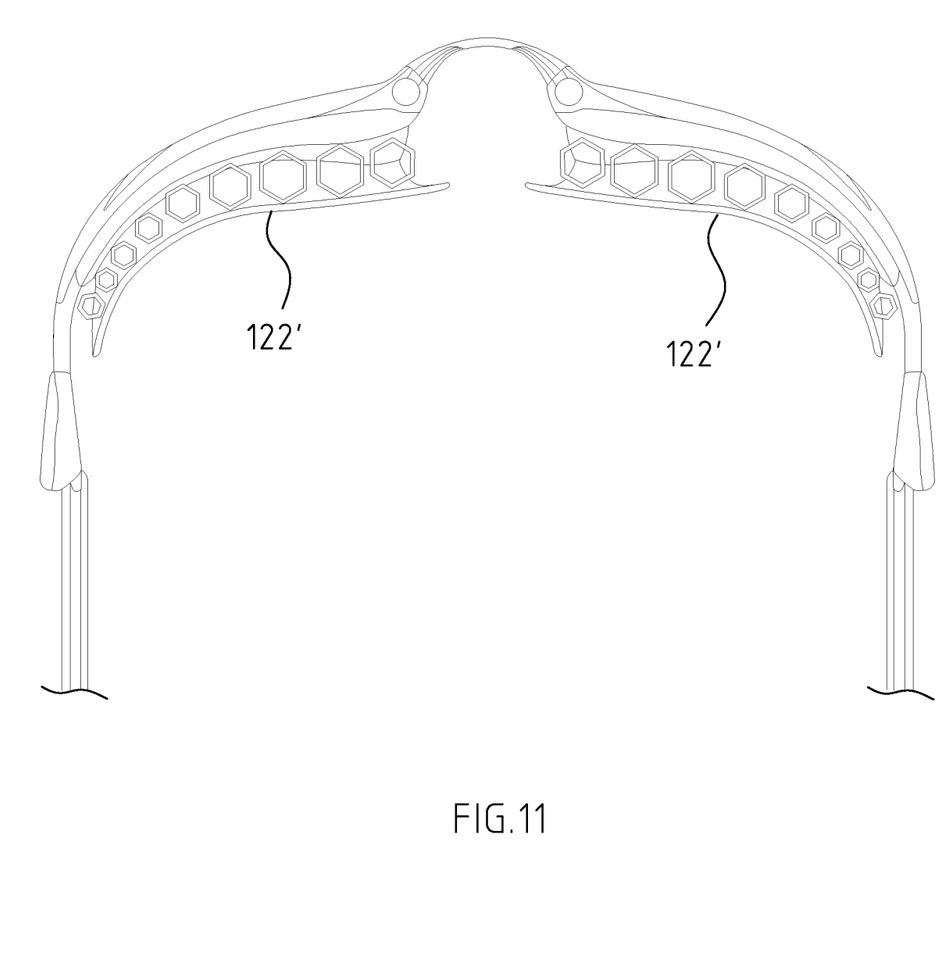

Please refer to FIG. 7 which is a perspective view of the cushion pad assembled on the frame of swimming goggles according to a second embodiment of the present invention disclosure. As shown in the figure, the cushion pad 1' in this embodiment also comprises a connecting portion 11' and a face-attaching portion 12'. The connecting portion 11' has an inner peripheral surface 111' and an outer peripheral surface 112'. The face-attaching portion 12' has an outer ring surface 121' and an inner ring surface 122'. The difference between this embodiment and the first embodiment is that is this embodiment, the design in the shape of the buffering bodies 3' is different. As shown in FIG. 8 FIG. 10 and FIG. 11, each of the buffering bodies 3' assembled with the frame of the swimming goggles is formed by a first supporting member 31', a second supporting member 32', and a plurality of joints 33' jointly form the buffering bodies 3' which are hexagonal from the side view perspective, each three sides of a hexagonal buffering body 3' forms a supporting member, so that the hexagonal buffering body 3' has a first supporting member 31' and a second supporting member 32' with a plurality of joints 33'_being formed. Further, a vertex 34' (i.e., a joint) and the other vertex 34" on the opposite side of the hexagonal buffering body 3' are respectively connected with the outer peripheral surface 112' of the connecting portion 11' and the outer ring surface 121' of the face-attaching portion 12'.

Similarly, in the above structure, with the aid of the first supporting member 31', the second supporting member 32' and the joint 33' of each of the buffering bodies 3' conforming to the contour of outer periphery of the eye socket, different squeezing and adsorption forces upon wearing the swimming goggles can be absorbed, in order to reduce an impact on contour of the outer periphery of the eye socket and thus prevent water seepage.

In view of the above, the cushion pad provided by the present invention disclosure can indeed achieve the purpose of creation and therefore meet the requirements of the Patent Act. However, what is illustrated above is merely preferred embodiments of the present invention disclosure. Various modifications and changes made according to the present invention disclosure shall fall within the claimed scope of the present invention application.

What is claimed is:

1. A cushion pad, assembled on a frame of swimming goggles, wherein the cushion pad comprises a connecting portion and a face-attaching portion, the connecting portion has an inner peripheral surface and an outer peripheral surface, the inner peripheral surface being provided with a groove for assembling with the frame of the swimming goggles; the face-attaching portion having an outer ring surface and an inner ring surface, the outer ring surface of the face-attaching portion being connected with the outer peripheral surface of the connecting portion, the inner ring surface of the face-attaching portion being arranged to contact an outer periphery of the eye socket of a wearer, and wherein:
   a plurality of independent buffering bodies are provided between the outer peripheral surface of the connecting portion and the outer ring surface of the face-attaching portion, wherein each of the buffering bodies is jointly composed of a first supporting member, a second supporting member and a joint at an intersection of the first supporting member and the second supporting member; wherein a buffering spring force between the cushion pad and the outer periphery of the eye socket of the wearer is configured to vary along different contact points on the outer periphery of the eye socket due to independent actions of each of the buffering bodies;
   wherein the first supporting member, the second supporting member and the joint of each of the buffering bodies are arranged to absorb force from the squeezing and deforming of a plurality of pressure-receiving spots on the inner ring surface of the face-attaching portion in order to reduce an impact on a contour of the outer periphery of the eye socket of the wearer, and to prevent water seepage;
   wherein each of the buffering bodies is formed by the first supporting member, the second supporting member and the joint, with each buffering body being V-shaped in a sideview, with the first supporting member and the second supporting member respectively forming two wings of each buffering body, with the joint being an intersection point of the two wings, and with the first supporting member and the second supporting member of each of the buffering bodies being connected with the outer peripheral surface of the connecting portion, and the outer ring surface of the face-attaching portion, respectively;
   wherein the first supporting member and second supporting member of each of the buffering bodies are arranged to be different in length so as to conform to the depth and height of the outer periphery of the eye socket of the wearer, the outer periphery of the eye socket of the wearer being wavy curved in shape, in which the side of each of the buffering bodies near the outer peripheral surface of the connecting portion is shorter than the side of each of the buffering bodies near a side of the outer ring surface of the face-attaching portion, so as to conform to the contour of the outer periphery of the eye socket of the wearer, and absorb squeezing and adsorption forces between the cushion pad and the outer periphery of the eye socket of the wearer, when worn.

2. The cushion pad of claim 1, wherein the inner ring surface of the face-attaching portion has a wavy curve shape that is configured to conform to a depth and height of the outer periphery of the eye socket of the wearer, and wherein a first peak of the inner ring surface corresponds to a center of a brow, a second peak of the inner ring surface corresponds to a cheekbone, a first valley of the inner ring surface corresponds to an eye corner, and a second valley of the inner ring surface corresponds to a nose bridge, so that a slope which has a wavy curved shape is formed along the first peak at the center of the brow, the first valley at the eye corner, and the second peak at the cheekbone to the second valley of the nose bridge, when worn.

3. The cushion pad of claim 1, wherein the slope of the shorter side of each of the buffering bodies is steeper and thicker than that of the longer side of each of the buffering bodies.

4. The cushion pad of claim 1, wherein a sideview of each of the buffering bodies presents a V-shaped pattern which is thickest at the joint and gradually thinner extending from the joint to a terminal end of each of the two wings.

5. The cushion pad of claim 1, wherein openings of each of the buffering bodies are arranged off an axis determined by a line connecting the center of the brow and the cheekbone of the wearer, when worn.

6. The cushion pad of claim 1, wherein the connecting portion and the face-attaching portion of the cushion pad are made of thermoplastic rubber (TPR) or silicone, and the material of the connecting portion is harder than that of the face-attaching portion.

\* \* \* \* \*